(12) United States Patent
Vidlund (10) Patent No.: US 11,006,939 B2
(45) Date of Patent: May 18, 2021

(54) INTRODUCER SHEATH WITH SEAL AND METHODS OF USING THE SAME

(71) Applicant: Tendyne Holdings, Inc., St. Paul, MN (US)

(72) Inventor: Zachary Vidlund, Minneapolis, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 242 days.

(21) Appl. No.: 16/212,781

(22) Filed: Dec. 7, 2018

(65) Prior Publication Data

US 2019/0175159 A1 Jun. 13, 2019

Related U.S. Application Data

(60) Provisional application No. 62/596,469, filed on Dec. 8, 2017.

(51) Int. Cl.
*A61B 17/00* (2006.01)
*A61M 29/02* (2006.01)
(Continued)

(52) U.S. Cl.
CPC ...... *A61B 17/0057* (2013.01); *A61B 17/3421* (2013.01); *A61M 25/0662* (2013.01);
(Continued)

(58) Field of Classification Search
CPC ............ A61B 17/0057; A61B 17/3423; A61B 17/3439; A61B 17/3421;
(Continued)

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| DE | 102005003632 A1 | 8/2006 |
| EP | 1129744 A1 | 9/2001 |

(Continued)

OTHER PUBLICATIONS

International Search Report for Application No. PCT/US2016/049888 dated Dec. 12, 2016.

(Continued)

*Primary Examiner* — Ashley L Fishback
(74) *Attorney, Agent, or Firm* — Lerner, David, Littenberg, Krumholz & Mentlik, LLP (57) ABSTRACT

In some embodiments, an apparatus includes an introducer sheath and a dilator. The introducer sheath can include a body portion and a tip portion. The body portion can be coupled to the tip portion via a seal portion. The dilator can be configured to be inserted into a lumen defined by the introducer sheath such that the dilator can engage with the tip portion and translate the tip portion relative to the body portion such that the tip portion moves the seal portion from a biased neutral configuration to an extended configuration for delivery of the apparatus to a location in a patient's body. The seal portion can have a larger outermost diameter in the neutral configuration than in the extended configuration.

18 Claims, 9 Drawing Sheets

(51) Int. Cl.
*A61M 25/06* (2006.01)
*A61B 17/34* (2006.01)

(52) U.S. Cl.
CPC ... *A61M 29/02* (2013.01); *A61B 2017/00646* (2013.01); *A61B 2017/00867* (2013.01); *A61B 2017/00986* (2013.01); *A61B 2017/3425* (2013.01); *A61B 2017/3484* (2013.01); *A61B 2017/3488* (2013.01)

(58) Field of Classification Search
CPC ........... A61B 2017/00575; A61B 2017/00597; A61B 2017/0061; A61B 2017/00659; A61B 2017/00637; A61B 2017/00615; A61B 2017/00646; A61B 2017/00986; A61B 2017/348; A61B 2017/3482; A61B 2017/3484; A61B 2017/3486; A61B 2017/3488; A61B 2017/3425; A61B 2017/3427; A61B 2017/3435; A61B 2017/3441; A61M 25/0662
See application file for complete search history.

(56) References Cited

U.S. PATENT DOCUMENTS

| | | | |
|---|---|---|---|
| 5,078,720 A | 1/1992 | Burton et al. | |
| 5,201,756 A | 4/1993 | Horzewski et al. | |
| 5,256,150 A | 10/1993 | Quiachon et al. | |
| 5,295,994 A * | 3/1994 | Bonutti | A61B 17/0218 604/103 |
| 5,336,176 A * | 8/1994 | Yoon | A61B 17/3417 604/164.11 |
| 5,395,349 A | 3/1995 | Quiachon et al. | |
| 5,415,664 A | 5/1995 | Pinchuk | |
| 5,484,418 A | 1/1996 | Quiachon et al. | |
| 5,484,444 A | 1/1996 | Braunschweiler et al. | |
| 5,591,228 A | 1/1997 | Edoga | |
| 5,653,697 A | 8/1997 | Quiachon et al. | |
| 5,662,614 A | 9/1997 | Edoga | |
| 5,702,418 A | 12/1997 | Ravenscroft | |
| 5,707,385 A | 1/1998 | Williams | |
| 5,746,766 A | 5/1998 | Edoga | |
| 5,766,203 A | 6/1998 | Imran et al. | |
| 5,824,041 A | 10/1998 | Lenker et al. | |
| 5,843,160 A | 12/1998 | Rhodes | |
| 5,843,167 A | 12/1998 | Dwyer et al. | |
| 5,875,782 A * | 3/1999 | Ferrari | A61B 17/0206 128/898 |
| 5,924,424 A | 7/1999 | Stevens et al. | |
| 5,928,246 A | 7/1999 | Gordon et al. | |
| 5,935,122 A | 8/1999 | Fourkas et al. | |
| 5,968,068 A | 10/1999 | Dehdashtian et al. | |
| 5,980,533 A | 11/1999 | Holman | |
| 5,997,508 A | 12/1999 | Lunn et al. | |
| 6,027,508 A | 2/2000 | Ren et al. | |
| 6,027,509 A | 2/2000 | Schatz et al. | |
| 6,077,297 A | 6/2000 | Robinson et al. | |
| 6,090,072 A | 7/2000 | Kratoska et al. | |
| 6,143,016 A | 11/2000 | Bleam et al. | |
| 6,149,574 A | 11/2000 | Trauthen et al. | |
| 6,162,237 A | 12/2000 | Chan | |
| 6,183,443 B1 | 2/2001 | Kratoska et al. | |
| 6,197,016 B1 | 3/2001 | Fourkas et al. | |
| 6,269,819 B1 | 8/2001 | Oz et al. | |
| 6,306,141 B1 | 10/2001 | Jervis | |
| 6,391,050 B1 | 5/2002 | Broome | |
| 6,468,299 B2 | 10/2002 | Stack et al. | |
| 6,623,518 B2 | 9/2003 | Thompson et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,803,185 B2 | 9/2010 | Gabbay | |
| 7,993,356 B2 * | 8/2011 | Rapacki | A61B 17/3468 606/153 |
| 8,562,680 B2 | 10/2013 | Hays et al. | |
| 8,652,204 B2 | 2/2014 | Quill et al. | |
| 8,668,668 B2 | 3/2014 | Bishop et al. | |
| 8,690,936 B2 | 4/2014 | Nguyen et al. | |
| 8,728,153 B2 | 5/2014 | Bishop et al. | |
| 8,747,470 B2 | 6/2014 | Beck, Jr. et al. | |
| 8,784,434 B2 | 7/2014 | Rosenbluth et al. | |
| 8,790,387 B2 | 7/2014 | Nguyen et al. | |
| 8,801,744 B2 | 8/2014 | McCrystle et al. | |
| 8,801,779 B2 | 8/2014 | Seguin et al. | |
| 8,814,832 B1 | 8/2014 | Al-Rashdan et al. | |
| 8,840,663 B2 | 9/2014 | Salahieh et al. | |
| 8,900,191 B2 | 12/2014 | Lenker et al. | |
| 8,900,214 B2 | 12/2014 | Nance et al. | |
| 8,956,410 B2 | 2/2015 | Donnelly et al. | |
| 9,078,682 B2 | 7/2015 | Lenker et al. | |
| 9,119,738 B2 | 9/2015 | Fish | |
| 9,125,728 B2 | 9/2015 | Angel et al. | |
| 9,173,751 B2 | 11/2015 | Schmid et al. | |
| 9,265,602 B2 | 2/2016 | Beck, Jr. et al. | |
| 9,301,840 B2 | 4/2016 | Nguyen et al. | |
| 9,301,841 B2 | 4/2016 | Nguyen et al. | |
| 9,320,846 B2 | 4/2016 | Burns et al. | |
| 9,370,438 B2 | 6/2016 | Ginn | |
| 9,387,314 B2 | 7/2016 | Bishop et al. | |
| 9,421,080 B2 | 8/2016 | Angel et al. | |
| 9,427,300 B2 | 8/2016 | Angel et al. | |
| 9,433,766 B2 | 9/2016 | Bishop et al. | |
| 9,439,653 B2 | 9/2016 | Avneri et al. | |
| 9,440,054 B2 | 9/2016 | Bishop et al. | |
| 9,788,944 B2 | 10/2017 | Daly et al. | |
| 2003/0050694 A1 | 3/2003 | Yang et al. | |
| 2004/0199202 A1 * | 10/2004 | Dubrul | A61B 90/39 606/200 |
| 2004/0210304 A1 | 10/2004 | Seguin et al. | |
| 2005/0085746 A1 | 4/2005 | Adams et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2006/0041270 A1 | 2/2006 | Lenker et al. | |
| 2006/0074484 A1 | 4/2006 | Huber | |
| 2006/0106415 A1 | 5/2006 | Gabbay | |
| 2006/0135981 A1 | 6/2006 | Lenker et al. | |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2008/0071369 A1 | 3/2008 | Tuval et al. | |
| 2008/0147182 A1 | 6/2008 | Righini et al. | |
| 2009/0054975 A1 | 2/2009 | del Nido et al. | |
| 2010/0004740 A1 | 1/2010 | Seguin et al. | |
| 2010/0286768 A1 | 11/2010 | Alkhatib | |
| 2010/0298931 A1 | 11/2010 | Quadri et al. | |
| 2011/0114700 A1 | 5/2011 | Baxter, III et al. | |
| 2011/0224678 A1 | 9/2011 | Gabbay | |
| 2011/0257734 A1 | 10/2011 | Chalekian | |
| 2011/0282287 A1 | 11/2011 | Chalekian | |
| 2012/0109281 A1 | 5/2012 | Papp | |
| 2013/0178711 A1 | 7/2013 | Avneri et al. | |
| 2013/0211324 A1 | 8/2013 | Voss et al. | |
| 2013/0297011 A1 | 11/2013 | Morris et al. | |
| 2015/0073538 A1 * | 3/2015 | Thomas | A61F 2/2418 623/2.11 |

(56) References Cited

U.S. PATENT DOCUMENTS

2016/0095622 A1  4/2016  Clancy et al.
2017/0014157 A1  1/2017  Coyle et al.

FOREIGN PATENT DOCUMENTS

| EP | 1157673 A2 | 11/2001 |
| EP | 1759645 A1 | 3/2007 |
| EP | 1926455 A2 | 6/2008 |
| WO | 02067782 A2 | 9/2002 |
| WO | 07071436 A2 | 6/2007 |
| WO | 2008070797 A2 | 6/2008 |
| WO | 2009097650 A1 | 8/2009 |
| WO | 10051025 A1 | 5/2010 |
| WO | 2010081105 A1 | 7/2010 |
| WO | 10087975 A1 | 8/2010 |
| WO | 2014124283 A1 | 8/2014 |
| WO | 2016144115 A1 | 9/2016 |
| WO | 2016196933 A1 | 12/2016 |
| WO | 2017040774 A1 | 3/2017 |

OTHER PUBLICATIONS

Ruiz, Carlos, Overview of PRE-CE Mark Transcatheter Aortic Valve Technologies, Euro PCR dated May 25, 2010.
Percutaneous aortic valve replacement: resection before implantation, 836-840, Quaden, Rene et al., European J. of Cardio-thoracic Surgery, 27 (2005).
International Search Report including Written Opinion for Application No. PCT/US2018/031011 dated Jul. 31, 2018.
Extended European Search Report for Application No. EP14189214.1 dated Mar. 3, 2015.
International Search Report and Witten Opinion for PCT/US2018/030633, dated Sep. 28, 2018.

* cited by examiner

INTRODUCER SHEATH WITH SEAL AND METHODS OF USING THE SAME

CROSS-REFERENCE TO RELATED APPLICATIONS

This application claims the benefit of the filing date of U.S. Provisional Patent Application No. 62/596,469 filed Dec. 8, 2017, the disclosure of which is hereby incorporated herein by reference.

BACKGROUND OF THE DISCLOSURE

Embodiments are described herein that relate to devices and methods for use in sealing a puncture site of the body of a patient, and particularly to devices and methods for providing access to a vasculature or a heart at a puncture site to deliver a procedural device, and sealing the puncture site during delivery of the procedural device to the vasculature or heart.

Some known introducer sheaths have been used to access a vasculature or a heart via a puncture site. Some known introducer sheaths can provide access to the vasculature or the heart for delivery of procedural devices or insertion of medical instruments. However, known introducer sheaths have various shortcomings. For example, when accessing a heart with an introducer sheath to deliver various procedural devices or instruments to the heart, blood can undesirably leak around the introducer sheath and out of the access site. In addition, when accessing a vasculature or a heart it is desirable to have a small diameter introducer sheath to reduce the size of the puncture site.

Thus, a need exists for devices and methods for providing access to a vasculature or a heart with a small diameter device to deliver various procedural devices and instruments, and sealing the puncture site during the delivery.

BRIEF SUMMARY

Apparatus and methods are described herein for use in providing access to a vasculature or heart of a patient and sealing the puncture site in the patient. In some embodiments, an apparatus includes an introducer sheath and a dilator. The introducer sheath can include a body portion and a distal tip portion. The body portion can be coupled to the distal tip portion via a seal portion. The dilator can be configured to be inserted into a lumen defined by the introducer sheath such that the dilator can engage with the distal tip portion and translate the distal tip portion relative to the body portion such that the seal portion is moved from a neutral configuration to an extended configuration. The seal portion can have a larger outermost diameter in the neutral configuration than in the extended configuration. The seal portion can be used to prevent blood leakage around the introducer sheath when disposed at a puncture site.

DETAILED DESCRIPTION

Apparatus and methods are described herein for use in sealing a puncture site, such as, for example, a puncture site where an introducer sheath has been disposed in a vasculature or in the apex of a heart of a patient. In some embodiments, an apparatus includes an introducer sheath and a dilator. The introducer sheath can include a body portion and a distal tip portion. The body portion can be coupled to the distal tip portion via a seal portion. The dilator can be configured to be inserted into a lumen defined by the introducer sheath such that the dilator can engage with the distal tip portion and translate the distal tip portion relative to the body portion such that the distal tip portion pulls the seal portion from a neutral configuration to an extended configuration. The seal portion can have a larger outermost diameter in the neutral configuration than in the extended configuration. The seal portion can be used to prevent blood leakage around the introducer sheath when disposed at a puncture site and in the neutral configuration.

Figure 1A:
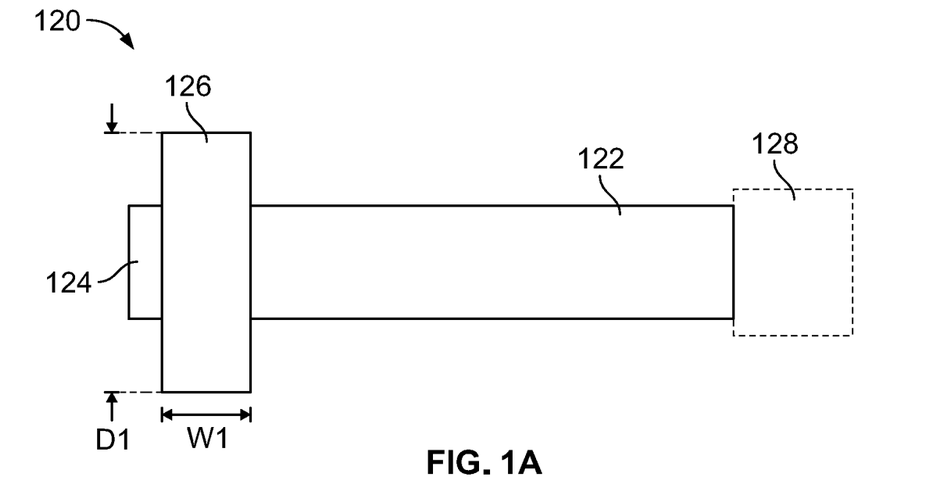
FIG. 1A is a schematic illustration of an introducer sheath in a neutral configuration, according to an embodiment.

FIG. 1A is a schematic illustration of an introducer sheath 120 in a neutral configuration. The introducer sheath 120 can include a body portion 122, a distal tip portion 124, and a seal portion 126. The seal portion 126 can be coupled between the body portion 122 and the distal tip portion 124. The introducer sheath 120 can also optionally include a handle portion 128. The body portion 122, the seal portion 126, and the distal tip portion 124 can collectively define a continuous inner lumen configured to receive, for example, a dilator or any other suitable medical instrument. The handle portion 128 can be disposed on the proximal end of the body portion 122 and can define an opening to the lumen defined by the body portion 122, the seal portion 126, and the distal tip portion 124. The outer diameter of the body portion 122 can be various sizes to meet a particular need. In some embodiments, the outer diameter of the body portion 122 can be, for example, 8 French or smaller. In some embodiments, a proximal end portion of the introducer sheath 120 can include a hemostasis valve as described below for introducer sheath 520.

Figure 1B:
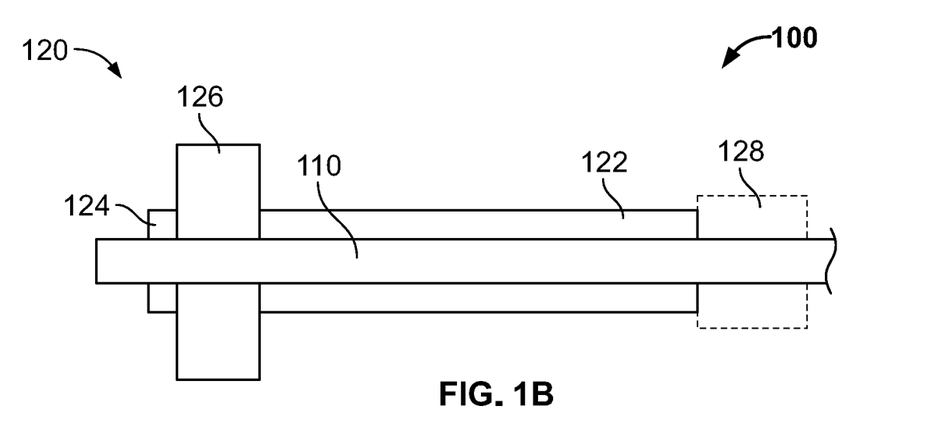
FIG. 1B is a schematic illustration of a sealing introducer assembly including the introducer sheath of FIG. 1A, according to an embodiment, shown in a first configuration.
Figure 1C:
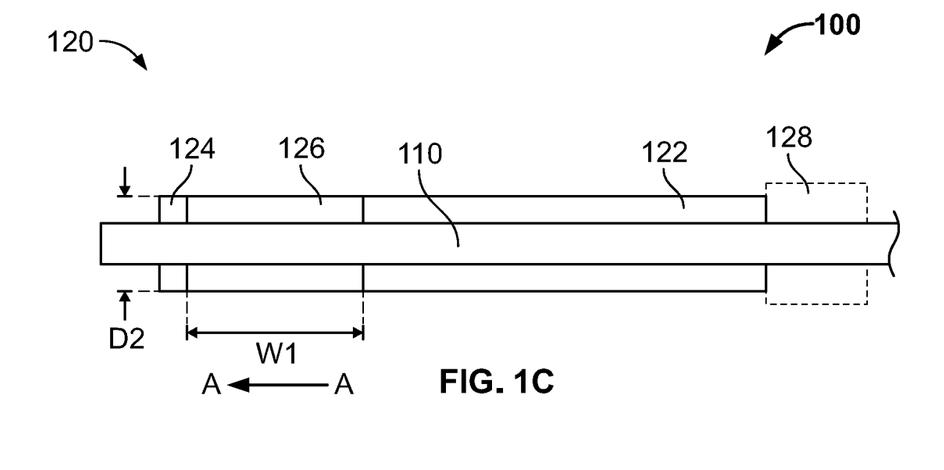
FIG. 1C is a schematic illustration of the sealing introducer assembly of FIG. 1B in an extended second configuration.

The seal portion 126 can have a neutral configuration, as shown in FIG. 1A and an extended configuration as shown in FIG. 1C. The seal portion 126 can be biased to the neutral position. In other words, when the seal portion 126 is not influenced by a stretching or extending force (as described in more detail below), the seal portion 126 can transition into or remain in the neutral configuration shown in FIG. 1A. In such a configuration, the seal portion 126 can have a first diameter D1 and a first width W1. When the seal portion 126 is under the influence of a stretching or extending force, as described in more detail below, the seal portion 126 can have a second diameter D2 that is smaller than the first diameter D1 and a second width W2 that is larger than the first width W1 (as shown in FIG. 1C). The seal portion 126 can be structured such that the seal portion 126 is, for example, disc-shaped in the neutral configuration and shaped as an elongated tube in the extended configuration. In some embodiments, the seal portion 126 can be formed of a material that can cause the seal portion 126 to be biased toward the neutral configuration such as a shape memory material, for example, a nickel titanium alloy (also referred to as Nitinol). In some embodiments, the seal portion 126 is formed with a braided or mesh material. The material and configuration of the seal portion 126 allows the introducer sheath 120 to maintain a small outer diameter. In other words, having an expandable seal portion 126 as described herein does not result in the introducer sheath 120 having a larger diameter. In some embodiments, the seal portion 126 can have an outer diameter when in the extended configuration that is the same size or smaller size than an outer diameter of the body portion 122.

Although the seal portion 126 is shown and described as being disc shaped when in the biased neutral configuration, in other embodiments, the seal portion 126 can have other shapes. For example, the seal portion 126 can be cylindrical, can have a double-disc shape, or a bell or hourglass shape, or any other shape that is suitable to assist in sealing and/or maintaining the introducer sheath 120 in position during a procedure. Although the introducer sheath 120 is shown and described as having a single sealing portion 126, in other embodiments, an introducer sheath 120 can include more than one sealing portion 126. For example, in some embodiments, and introducer sheath 120 can include two, three or four sealing portions 126, with each sealing portion separated by a portion of the body portion of the introducer sheath 120.

As shown in FIGS. 1B and 1C, the introducer sheath 120 can be included in a sealing introducer assembly 100. The sealing introducer assembly 100 can also include a dilator 110. The dilator 110 can be shaped and sized such that the dilator 110 can be inserted through the lumen defined by the introducer sheath 120 (i.e., the lumen defined by the body portion 122, the seal portion 126, and the distal tip portion 124). The dilator 110 can be configured to transition the seal portion 126 from the neutral configuration (shown in FIG. 1B) to the extended configuration (shown in FIG. 1C), thus transitioning the sealing introducer assembly 100 from a first configuration in which the introducer assembly 100 can seal a puncture site when in use (shown in FIG. 1B), to a second configuration (shown in FIG. 1C) in which the introducer assembly 100 can be delivered to a desired location within a patient's body (e.g., through a puncture site in a heart or vasculature). For example, as shown in FIG. 1B, the dilator 110 can be inserted into the lumen defined by the introducer sheath 120 and engage the distal tip portion 124 as described in more detail below with reference to specific embodiments. As shown in FIG. 1C, the dilator 110 can be further extended in the direction of arrow AA such that the dilator 110 translates the distal tip portion 124 in the direction of arrow AA relative to the body portion 122, causing the seal portion 126 to transition from the neutral configuration shown in FIGS. 1A and 1B to the extended configuration shown in FIG. 1C. Said another way, when the dilator 110 engages the distal tip portion 124, the translation of the dilator 110 distally, in the direction of arrow AA, relative to the introducer sheath 120 can stretch or unfold the seal portion 126 such that the seal portion 126 has the second width W2 and the second diameter D2. As described above, the second width W2 can be greater than the first width W1 and the second diameter D2 can be less than the first diameter D1.

The dilator 110 can reversibly engage with the distal tip portion 124 via any suitable engagement feature or features. In some embodiments, the engagement of the dilator 110 with the distal tip portion 124 is achieved by contact of the outer surface of the dilator 110 with an inner surface of the distal tip portion 124. For example, the distal tip portion 124 can have a smaller inner diameter than an outer diameter of the dilator 110. For example, the dilator 110 can have a tapered distal portion shaped and sized such that a proximal portion of the tapered distal portion has a greater outer diameter than an inner diameter of the distal tip portion 124. Thus, as the dilator 110 is translated in the direction of arrow AA, the proximal portion of the tapered distal portion of the dilator 110 can engage with the inner wall of the distal tip portion 124 and translate/move the distal tip portion 124 in the direction of arrow AA relative to the body portion 122, to transition the seal portion 126 to the extended configuration (and thus transition the sealing introducer assembly 100 to the second configuration).

In some embodiments, to engage the dilator 110 with the distal tip portion 124, the dilator 110 can include a first engagement feature configured to engage with a second corresponding engagement feature of the distal tip portion 124. The first engagement feature and/or the second engagement feature can each include, for example, a projection, a flange, and/or a lip. The first engagement feature and the second engagement feature can be aligned relative to each other such that, as the dilator 110 is advanced in the direction of arrow AA, the first engagement feature can engage with the second engagement feature of the distal tip portion 124 and move or translate the distal tip portion 124 relative to the body portion 122, transitioning the seal portion 126 to the extended configuration (and thus transitioning the sealing introducer assembly 100 to the second configuration).

In some embodiments, the distal tip portion 124 can have the same or a similar inner diameter and outer diameter as the body portion 122. In some embodiments, the distal tip portion 124 can have a smaller inner diameter and/or outer diameter than the body portion 122. Similarly, in some embodiments, when in the extended, delivery configuration, the seal portion 126 can have an outer diameter that is the same or similar as the outer diameter of the distal tip portion 124 and/or the body portion 122. In some embodiments, when in the extended, delivery configuration, the seal portion 126 can have a tapered shape extending from the distal tip portion 124 to the body portion 122.

To move the seal portion 126 back to its neutral configuration, the dilator 110 can be withdrawn proximally from the introducer sheath 120. For example, upon removal of the dilator 110 from the introducer sheath 120, the dilator 110 will disengage the distal tip portion 124 and allow the seal portion 126 to automatically return to the neutral configuration (as shown in FIG. 1A).

In use, the dilator 110 can be inserted into the lumen of the introducer sheath 120 and engage with the distal tip portion 124 as described above. The dilator 110 can be translated distally in the direction of arrow AA relative to the body portion 122 such that the seal portion 126 is transitioned into the extended configuration, and thus the sealing introducer assembly 100 is in the second configuration shown in FIG. 1C. When in the second configuration shown in FIG. 1C, the sealing introducer assembly 100 can then be inserted (e.g., over a guidewire) through a puncture site in a patient and used to introduce procedural devices or instruments into the patient's body. For example, the sealing introducer assembly 100 can be inserted through an apex of a heart of a patient or within a vasculature of a patient.

In one example use, with the sealing introducer assembly 100 in the extended second configuration, the sealing introducer assembly 100 can be inserted through the apex of the heart of a patient, and the distal tip portion 124 and the seal portion 126 can be positioned within the left ventricle of the heart. The dilator 110 can then be withdrawn from the introducer sheath 120 as described above. When the dilator 110 is withdrawn, the seal portion 126 can return to its neutral configuration shown in FIGS. 1A and 1B. In the neutral configuration, the diameter D1 of the seal portion 126 can be larger than a diameter of an opening (e.g., puncture site, access hole) formed in the apex of the heart by the sealing introducer assembly 100. Thus, after the seal portion 126 transitions to the neutral configuration, the introducer sheath 120 can be withdrawn proximally such that the seal portion 126 engages with the portion of the apex surrounding the opening inside the heart and seals the opening. With the introducer sheath 120 disposed in the heart and sealing the puncture site, one or more devices or instruments can be introduced into the heart as needed to perform a medical procedure within the heart. For example, in some embodiments, a prosthetic valve can be deployed within the heart and a valve positioning device can be inserted through the introducer sheath 120 to engage with and position and/or reposition the prosthetic valve within the heart (e.g., within the mitral annulus) as described, for example, in International Application No. PCT/US16/35719, entitled "Apical Control of Transvascular Delivery of Prosthetic Mitral Valve," filed Jun. 3, 2016 (hereinafter referred to as "the '719 application"), which is incorporated herein by reference in its entirety. In some embodiments, when a valve is delivered to the heart transfemorally, it is desirable to have a small puncture site at the apex of the heart to use for deploying an apical positioning device, as described in the '719 application, and/or any other suitable device. Thus, the introducer sheath 120 can have an outer diameter of no more than 8 French such that the puncture site size can be minimized.

After the procedure being performed is completed, to remove the introducer sheath 120 from engagement with the heart of the patient, the dilator 110 can be inserted and urged distally through the lumen of the introducer sheath 120 to transition the seal portion 126 to the extended configuration, as described above, such that the introducer sheath 120, in combination with the dilator 110 (e.g., the assembly 100), can be retracted from the heart. Although described as being inserted through and engaged with the apex of the heart, the sealing introducer assembly 100 can be inserted through and engaged with any suitable access location of a patient's body.

Figure 2A:
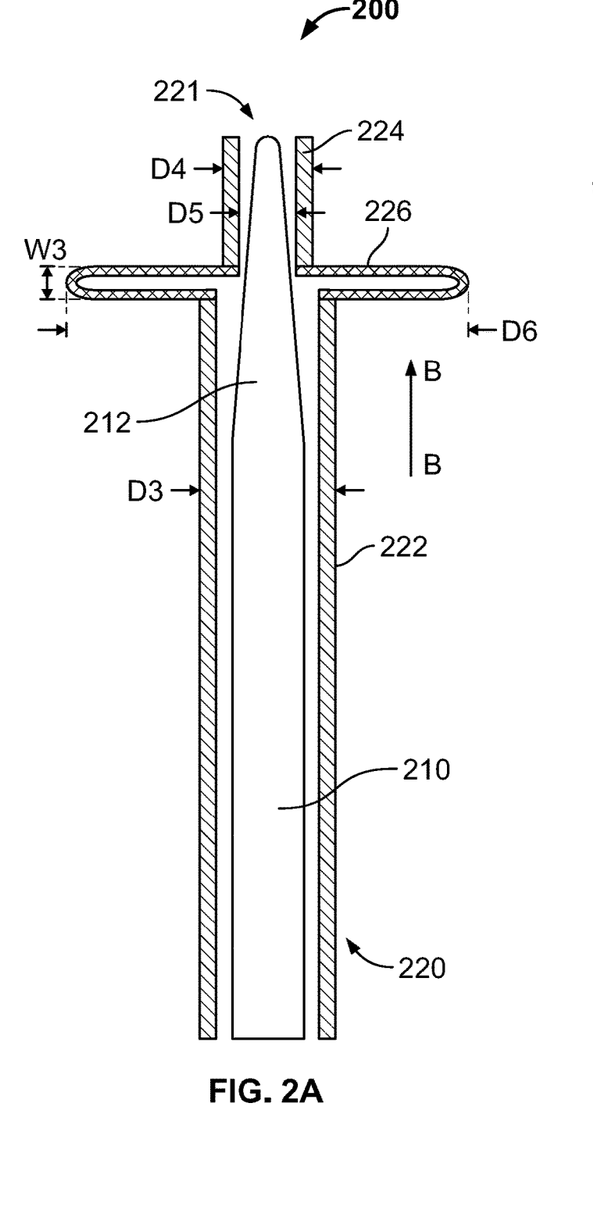
FIGS. 2A and 2B are cross-sectional schematic illustrations of a sealing introducer assembly in a first configuration and a second configuration, respectively, according to an embodiment.
Figure 2B:
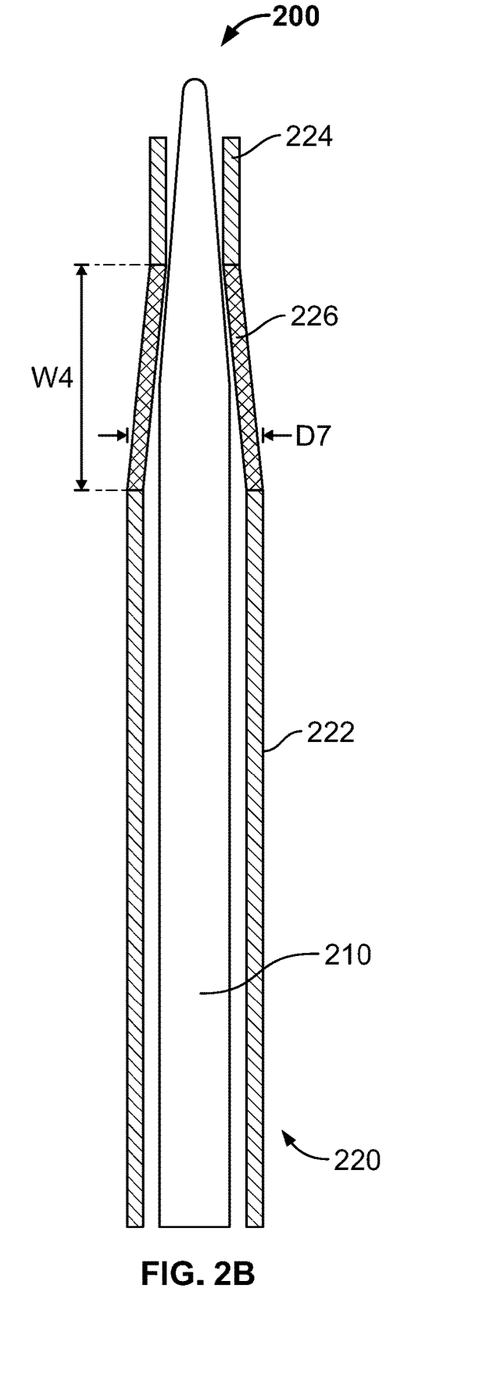

FIGS. 2A and 2B are cross-sectional schematic illustrations of a sealing introducer assembly 200 in a first configuration in which the sealing introducer assembly 200 can be used to seal a puncture site and a second configuration in which the sealing introducer assembly can be delivered to a desired location within a patient's body, respectively. The sealing introducer assembly 200 can be the same or similar in structure and/or function to any of the sealing introducer assemblies described herein, such as the sealing introducer assembly 100. For example, the sealing introducer assembly 200 can include an introducer sheath 220 and a dilator 210. The introducer sheath 220 can include a body portion 222, a distal tip portion 224, and a seal portion 226. The seal portion 226 can couple the body portion 222 to the distal tip portion 224. The body portion 222, the seal portion 226, and the distal tip portion 224 can collectively define a continuous inner lumen 221 configured to receive the dilator 210 or any other suitable medical instrument.

The seal portion 226 has a biased neutral configuration, as shown in FIG. 2A. In other words, when the seal portion 226 is not influenced by a stretching or extending force (e.g., due to engagement with the dilator 210) (as described in more detail below), the seal portion 226 can transition into or remain in the neutral configuration shown in FIG. 2A. In such a configuration, the seal portion 226 can have a larger outermost diameter and a smaller width than when the seal portion 226 is under the influence of an extending force. Specifically, the seal portion 226 can have a first width W3 and a first outermost diameter D6. The seal portion 226 can be structured such that the seal portion 226 is disc-shaped in the neutral configuration and shaped as an elongated, tapered tube in an extended configuration. In some embodiments, the seal portion 226 can be formed of a material that can cause the seal portion 226 to be biased toward the neutral configuration such as, for example, nickel titanium (also referred to as Nitinol).

As shown in FIGS. 2A and 2B, the dilator 210 can be shaped and sized such that the dilator 210 can be inserted through the lumen 221 defined by the introducer sheath 220. The dilator 210 can be configured to transition the seal portion 226 from the neutral configuration (shown in FIG. 2A) to the extended configuration (shown in FIG. 2B), thus transitioning the sealing introducer assembly 200 from the first configuration (shown in FIG. 2A) to the second configuration (shown in FIG. 2B). For example, as shown in FIG. 2A, the dilator 210 can be inserted into the lumen defined by the introducer sheath 220 and engaged with the distal tip portion 224. As shown in FIG. 2B, the dilator 210 can be further extended in the direction of arrow BB such that the dilator 210 translates the distal tip portion 224 in the direction of arrow BB relative to the body portion 222, causing the seal portion 226 to transition from the neutral configuration shown in FIG. 2A to the extended configuration shown in FIG. 2B. Said another way, when the dilator 210 engages the distal tip portion 224, the translation of the dilator 210 in the direction of arrow BB can stretch or unfold the seal portion 226 such that the seal portion 226 has a second width W4 and a second outermost diameter D7. The second width W4 can be greater than the first width W3 and the second outermost diameter D7 can be less than the first outermost diameter D6.

As shown in FIGS. 2A and 2B, the dilator 210 can reversibly engage with the distal tip portion 224. In this embodiment, the distal tip portion 224 can have a smaller inner diameter D5 than an outer diameter of the dilator 210. The dilator 210 can have a tapered distal portion 212 shaped and sized such that a proximal portion of the tapered distal portion 212 has a greater outer diameter than the inner diameter D5 of the distal tip portion 224. Thus, as the dilator 210 is translated in the direction of arrow BB, the proximal portion of the tapered distal portion 212 of the dilator 210 can engage with the inner wall of the distal tip portion 224 and translate/move the distal tip portion 224 in the direction of arrow BB relative to the body portion 222, transitioning the seal portion 226 to the extended configuration shown in FIG. 2B (and thus transitioning the sealing introducer assembly 200 to the second configuration).

To move the seal portion back to its neutral configuration, the dilator 210 can be withdrawn from the introducer sheath 220. For example, upon removal of the dilator 210 from the introducer sheath 220, the dilator 210 will disengage the distal tip portion 224 and allow the seal portion to automatically return to the neutral configuration (as shown in FIG. 2A).

Figure 3A:
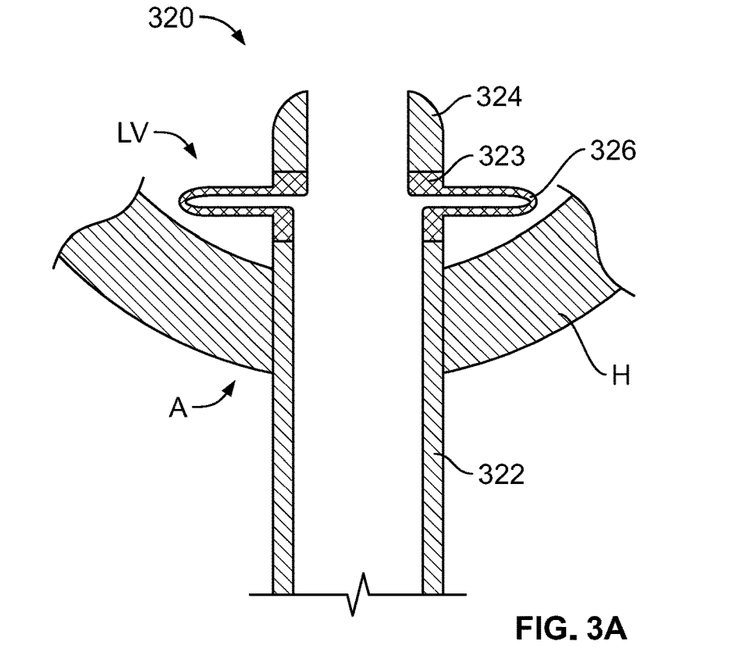
FIGS. 3A and 3B are cross-sectional schematic illustrations of a sealing introducer assembly in a first configuration and a second configuration disposed within a portion of a heart, respectively, according to an embodiment.
Figure 3B:
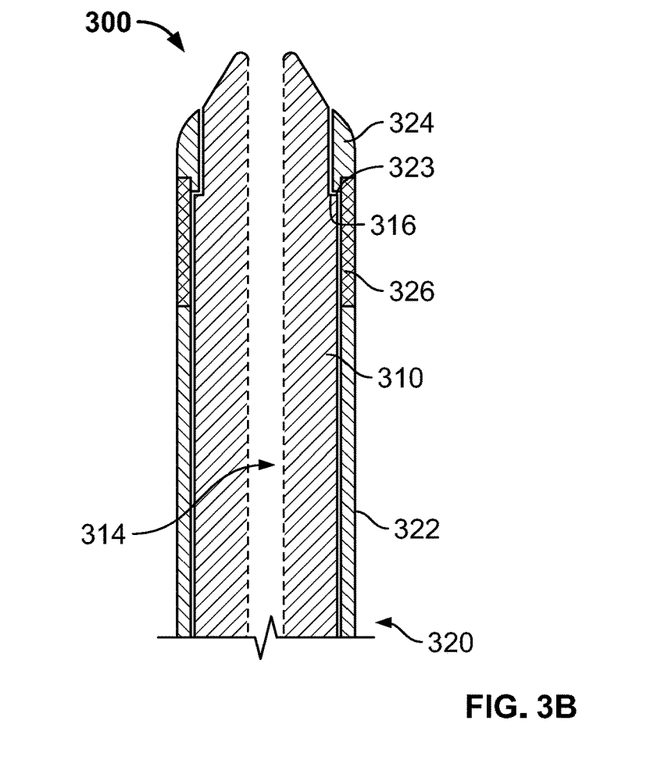

FIGS. 3A and 3B are cross-sectional schematic illustrations of a sealing introducer assembly 300 in a first configuration in which the sealing introducer assembly 300 can seal the puncture site through which it is inserted (shown inserted into a heart H in FIG. 3A), and a second configuration in which the sealing introducer assembly 300 can be delivered to a desired location within a patient's body, respectively. The sealing introducer assembly 300 can be the same or similar in structure and/or function to any of the sealing introducer assemblies described herein, such as the sealing introducer assembly 100. For example, the sealing introducer assembly 300 can include an introducer sheath 320 and a dilator 310. The introducer sheath 320 can include a body portion 322, a distal tip portion 324, and a seal portion 326. The seal portion 326 can couple the body portion 322 to the distal tip portion 324. The body portion 322, the seal portion 326, and the distal tip portion 324 can collectively define a continuous inner lumen configured to receive the dilator 310 or any other suitable medical instrument.

The seal portion 326 has a biased neutral configuration, as shown in FIG. 3A and an extended configuration as shown in FIG. 3B. More specifically, when the seal portion 326 is not influenced by an extending force (e.g., due to engagement with the dilator 310) (as described in more detail below), the seal portion 326 can transition into or remain in the neutral configuration shown in FIG. 3A. In such a configuration, the seal portion 326 can have a larger outermost diameter and a smaller width than when the seal portion 326 is under the influence of an extending force. The seal portion 326 can be structured such that the seal portion 326 is disc-shaped in the neutral configuration and shaped as an elongated tube in an extended configuration. In some embodiments, the seal portion 326 can be formed of a material that can cause the seal portion 326 to be biased toward the neutral configuration such as, for example, nickel titanium (also referred to as Nitinol).

As shown in FIG. 3B, the dilator 310 can be shaped and sized such that the dilator 310 can be inserted through the lumen defined by the introducer sheath 320. The dilator 310 can include a lumen 314 such that a medical instrument, such as a guidewire, can be threaded through the dilator 310. The dilator 310 can be configured to transition the seal portion 326 from the neutral configuration (shown in FIG. 3A) to the extended configuration (shown in FIG. 3B), thus transitioning the sealing introducer assembly 300 from the first configuration (shown in FIG. 3A) to the second configuration (shown in FIG. 3B). For example, as shown in FIG. 3B, the dilator 310 can be inserted into the lumen defined by the introducer sheath 320 and engage with the distal tip portion 324. As shown in FIG. 3B, the dilator 310 can be further extended such that the dilator 310 translates the distal tip portion 324 distally relative to the body portion 322, causing the seal portion 326 to transition from the neutral configuration shown in FIG. 3A to the extended configuration shown in FIG. 3B. Said another way, when the dilator 310 engages the distal tip portion 224, the translation of the dilator 310 can stretch or unfold the seal portion 326 such that the seal portion 326 has a smaller outermost diameter.

As shown in FIGS. 3A and 3B, the dilator 310 can reversibly engage with the distal tip portion 324. In this embodiment, the dilator 310 can include a first engagement feature 316 configured to engage with a corresponding second engagement feature 323 of the distal tip portion 324. The first engagement feature 316 can be a lip 316 formed between a larger outer diameter proximal portion and a relatively smaller outer diameter distal portion of the dilator 310. The second engagement feature 323 of the distal tip portion 324 can be a lip or flange formed on the distal tip portion 324 and shaped and sized such that as the dilator 310 is distally advanced, the first engagement feature 316 can engage with the second engagement feature 323 of the distal tip portion 324 and translate/move the distal tip portion 324 relative to the body portion 322, transitioning the seal portion 326 to the extended configuration (and thus transitioning the sealing introducer assembly 300 to the second configuration shown in FIG. 3B).

To move the seal portion 326 back to its neutral configuration, the dilator 310 can be withdrawn from the introducer sheath 320. For example, the sealing introducer assembly 300 can be introduced through the apex A of the heart H of a patient, as shown in FIG. 3B. When the seal portion 326 is disposed within the left ventricle LV, the dilator 310 can be withdrawn from the introducer sheath 320. Upon removal of the dilator 310 from the introducer sheath 320, the dilator 310 will disengage the distal tip portion 124 and allow the seal portion to automatically return to the neutral configuration (as shown in FIG. 3A). After the seal portion 326 transitions to the neutral configuration, the introducer sheath 320 can be pulled proximally such that the seal portion 326 engages with the portion of the apex A surrounding the opening and seals the opening. Although described as being inserted through and engaged with the apex A of the heart H, the sealing introducer assembly 300 can be inserted through and engaged with any suitable access location of a patient's body, such as the vasculature.

Figure 4A:
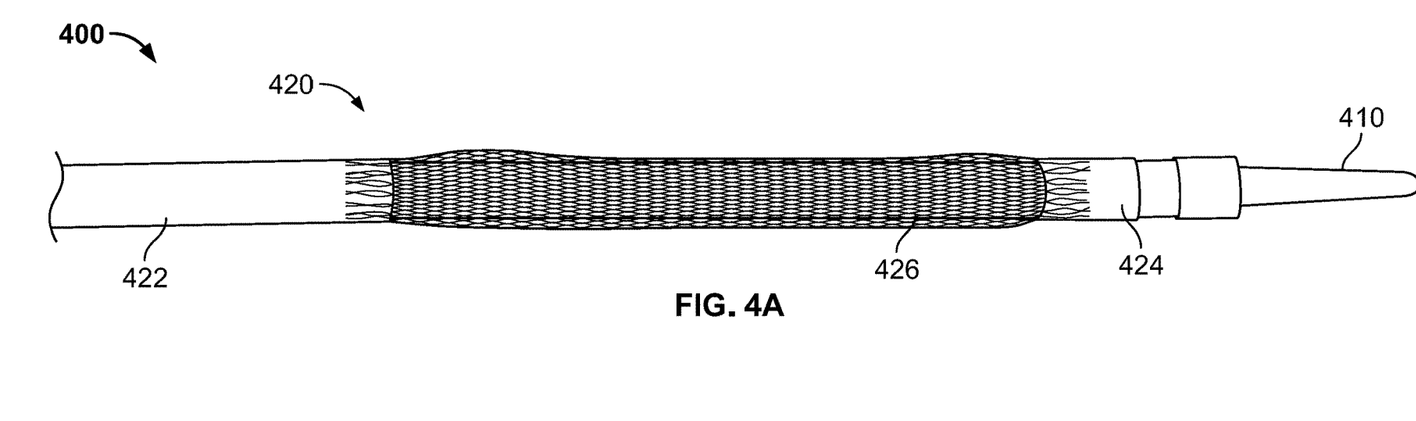
FIGS. 4A-4E are side views of a sealing introducer assembly as the sealing introducer assembly transitions from a second configuration to a first configuration, according to an embodiment.

FIGS. 4A-4E are side views of a sealing introducer assembly 400 in various configurations. The sealing introducer assembly 400 can be the same or similar in structure and/or function to any of the sealing introducer assemblies described herein, such as, for example, sealing introducer assembly 100. As shown in FIG. 4A, the sealing introducer assembly 400 can include an introducer sheath 420 and a dilator 410. The introducer sheath 420 can include a body portion 422, a distal tip portion 424, and a seal portion 426. The seal portion 426 can be coupled between the body portion 422 and the distal tip portion 424. The body portion 422, the seal portion 426, and the tip portion 424 can collectively define a continuous inner lumen configured to receive the dilator 410 or any other suitable medical instrument. The seal portion 426 can be the same or similar to any of the seal portions described herein, such as seal portion 126 and/or seal portion 226. For example, the seal portion 426 has a biased neutral configuration (shown in FIG. 4E) and can be moved to an extended configuration (shown in FIG. 4A). The seal portion 426 is shown as a braided tube of Nitinol wire. The seal portion 426 can also include a fluid impermeable layer (not shown for ease of illustration) covering the braided tube.

Figure 4B:
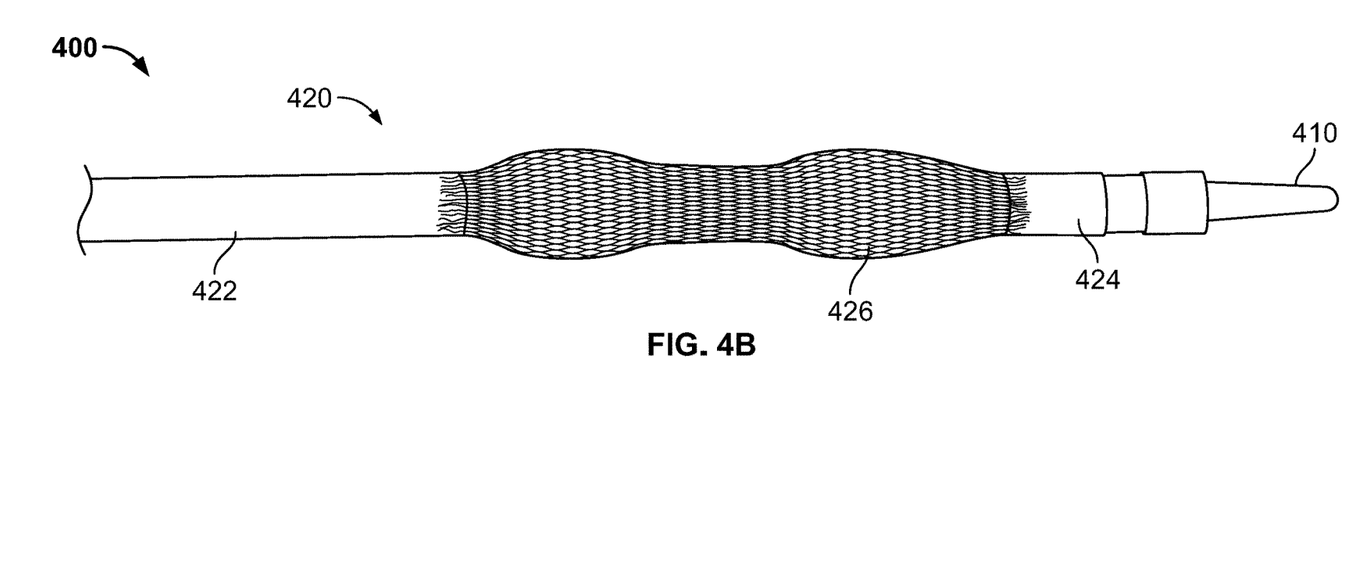
Figure 4C:
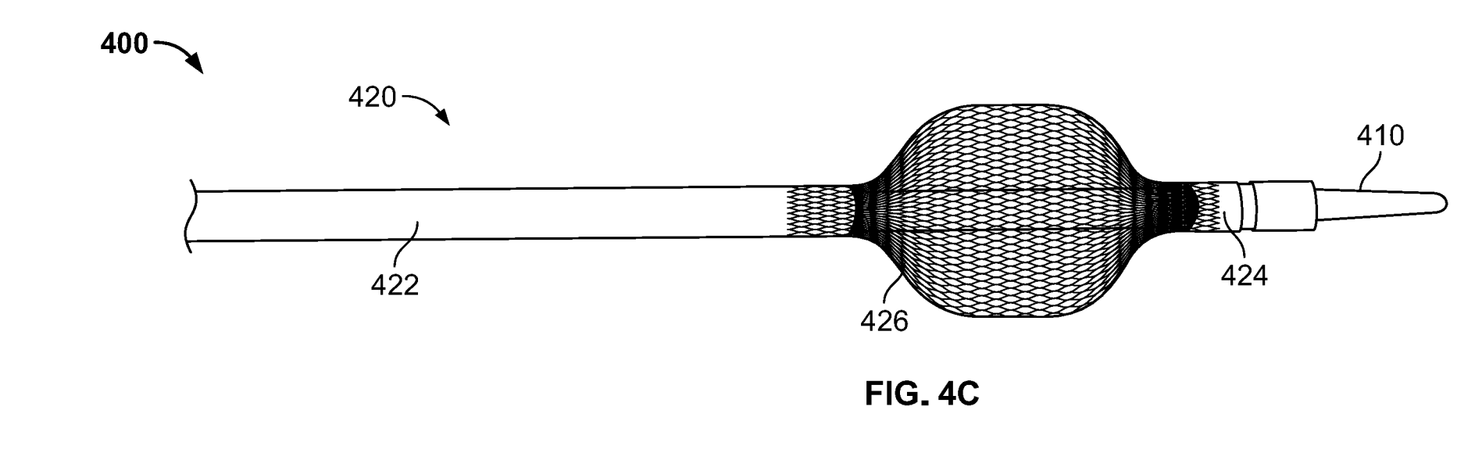
Figure 4D:
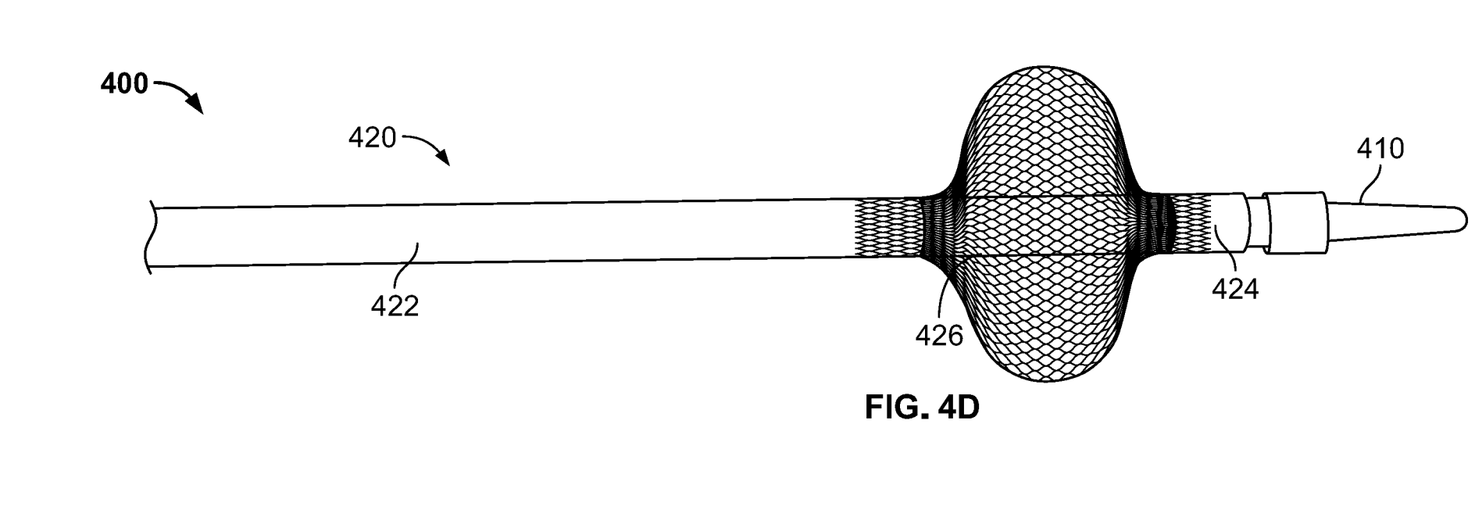
Figure 4E:
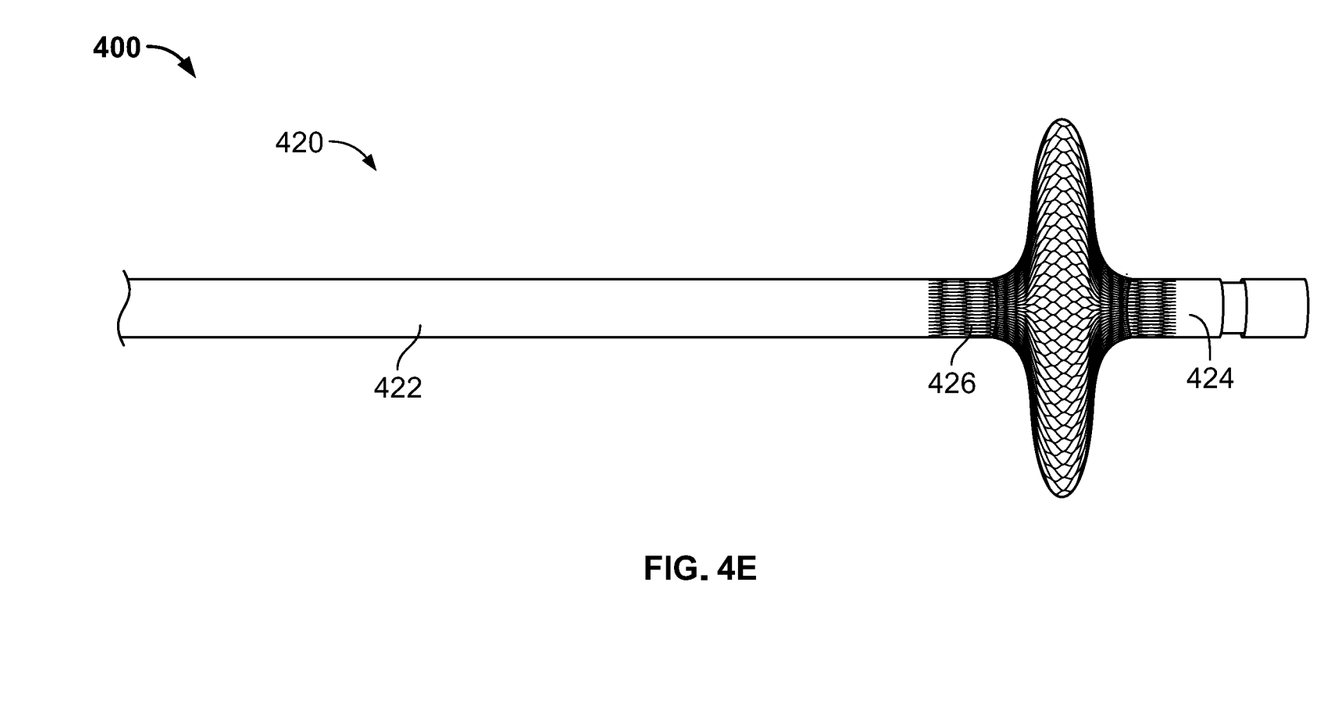

FIGS. 4A-4E show the sealing introducer assembly 400 as the sealing introducer assembly 400 progresses from a delivery or withdrawal configuration (also referred to herein as a second configuration) (FIG. 4A) to a biased neutral configuration (also referred to herein as a first configuration) (FIG. 4E). More specifically, FIG. 4A shows the dilator 410 fully engaged with the distal tip portion 424 of the introducer sheath 420 such that the dilator 410 moves the distal tip portion 424 distally relative to the body portion 422, maintaining the seal portion 426 in the extended configuration.

FIG. 4B shows the sealing introducer assembly 400 with the dilator 410 partially withdrawn and still engaged with the distal tip portion 424. As can be seen in FIG. 4B, the seal portion 426 is partially transitioned between the extended configuration and the neutral configuration. The seal portion 426 as shown in FIG. 4B has a shorter length and a larger outermost diameter than the seal portion 426 in the extended configuration shown in FIG. 4A.

FIG. 4C shows the sealing introducer assembly 400 with the dilator 410 further withdrawn in comparison with the configuration shown in FIG. 4B, but still engaged with the distal tip portion 424. As can be seen in FIG. 4C, the seal portion 426 is partially transitioned between the configuration shown in FIG. 4B and the neutral configuration. The seal portion 426 as shown in FIG. 4C has a shorter length and a larger outermost diameter than the seal portion 426 in the configuration shown in FIG. 4B.

FIG. 4D shows the sealing introducer assembly 400 with the dilator 410 further withdrawn in comparison with the configuration shown in FIG. 4C, but still engaged with the distal tip portion 424. As can be seen in FIG. 4D, the seal portion 426 is partially transitioned between the configuration shown in FIG. 4C and the neutral configuration. The seal portion 426 as shown in FIG. 4D has a shorter length and a larger outermost diameter than the seal portion 426 in the configuration shown in FIG. 4C.

FIG. 4E shows the introducer sheath 420 with the dilator 410 entirely removed. The seal portion 426 is in the neutral configuration. As shown in FIG. 4E, the seal portion 426 is disc-shaped in the neutral configuration and can be disposed in sealing relationship with, for example, an opening in the apex of a patient's heart.

Figures 5A, 5B:
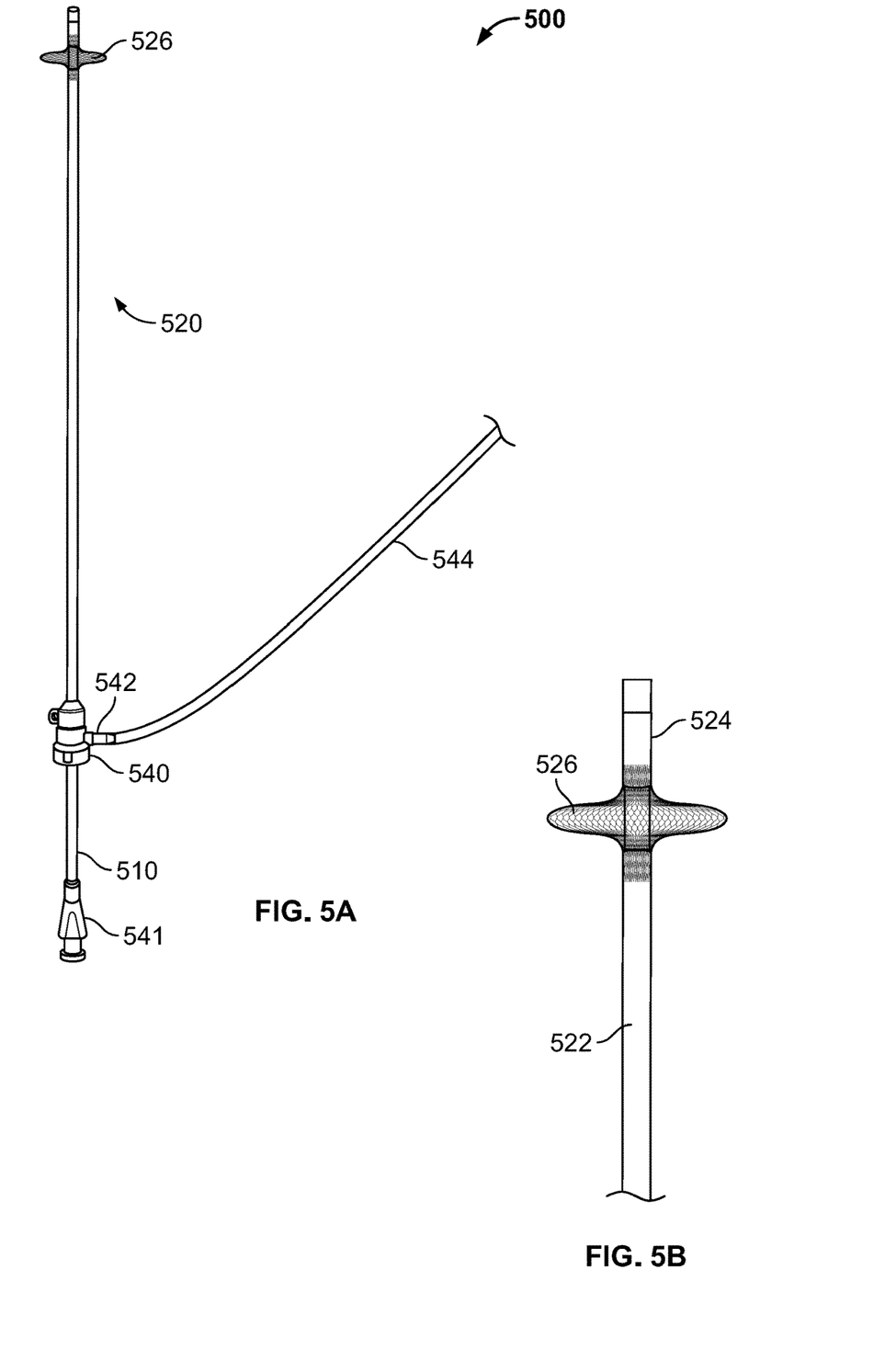
FIGS. 5A-5F are side views of a sealing introducer assembly in various configurations, according to an embodiment

FIGS. 5A-5F are side views of a sealing introducer assembly 500 in various configurations. The sealing introducer assembly 500 can be the same or similar in structure and/or function to any of the sealing introducer assemblies described herein, such as, for example, sealing introducer assembly 100. As shown in FIG. 5A, the sealing introducer assembly 500 can include an introducer sheath 520 and a dilator 510. As shown in FIG. 5B, which is a close up of the distal portion of the introducer sheath 520 as shown in FIG. 5A, the introducer sheath 520 can include a body portion 522, a distal tip portion 524, and a seal portion 526. The seal portion 526 can couple the body portion 522 to the distal tip portion 524. The body portion 522, the seal portion 526, and the distal tip portion 524 can collectively define a continuous inner lumen configured to receive the dilator 510 or any other suitable medical instrument. The seal portion 526 can be the same or similar in structure and/or function to any of the seal portions described herein, such as seal portion 126 and/or seal portion 226. For example, the seal portion 526 has a biased neutral configuration (shown in FIGS. 5A and 5B) and can be moved to an extended configuration (shown in FIGS. 5E and 5F). The seal portion 526 is shown as a braided tube of Nitinol wire. The seal portion 526 can also include a fluid impermeable layer (not shown for ease of illustration) covering the braided tube.

The introducer sheath 520 can include a hub 540 coupled to the body portion 522 through which the dilator 510 can be inserted. The hub 540 can include a hemostasis valve (e.g., a silicone hemostasis valve) to control the flow of fluid in a proximal direction during an interventional procedure. For example, the hemostasis valve can prevent blood from being lost through the sheath during a procedure. Additionally, the hub 540 can include a connector 542 defining an opening such that a tube 544 can be coupled to the handle 540 for fluid delivery through the introducer sheath 520. The dilator 510 can include a proximal handle portion 541. In use, the hub 540 and handle portion 541 can be used by a user to actuate the sealing introducer assembly 500.

Figure 5C:
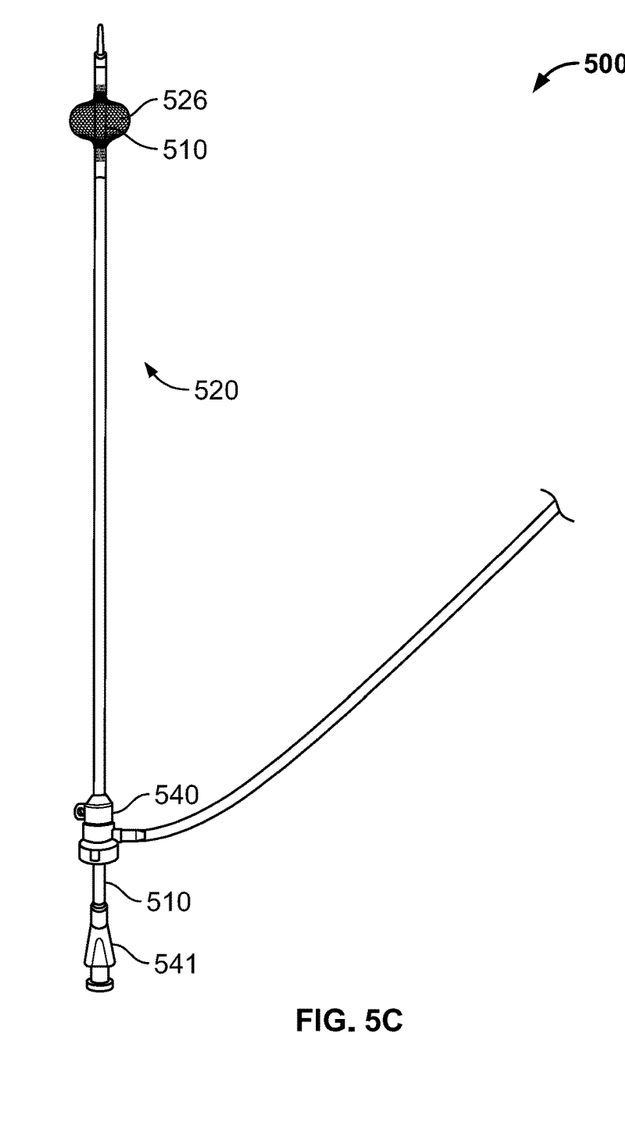
Figure 5D:
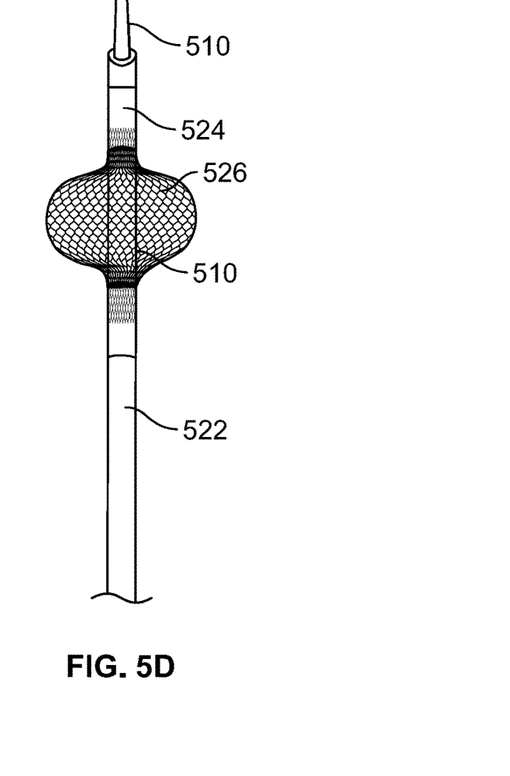
Figure 5E:
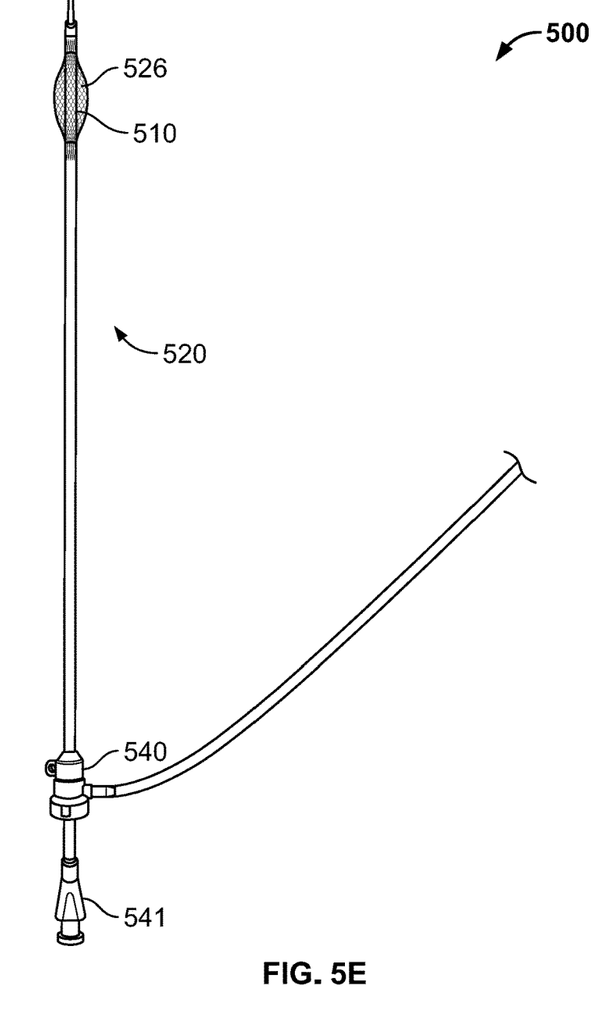
Figure 5F:
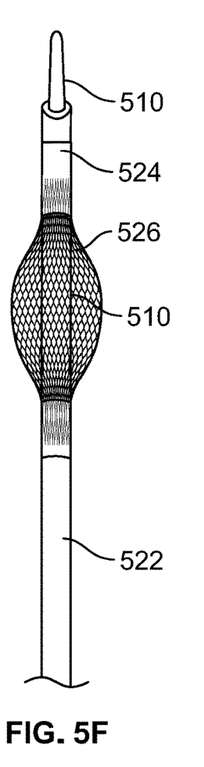

FIGS. 5A-5F show the sealing introducer assembly 500 as the sealing introducer assembly 500 progresses from a pre-delivery or a biased neutral configuration (also referred to herein as a first configuration) (FIG. 5A) to a delivery or withdrawal configuration (also referred to herein as a second configuration) (FIG. 5E). More specifically, FIGS. 5A and 5B show the dilator 510 retracted relative to the distal tip portion 524 of the introducer sheath 520 such that the seal portion 526 is in the neutral configuration. FIGS. 5C and 5D (FIG. 5D being a close up of the distal portion of the sealing introducer assembly 500 as shown in FIG. 5C) show the sealing introducer assembly 500 with the dilator 510 engaged with the distal tip portion 524 and partially extended relative to the body portion 522. In the partially transitioned configuration shown in FIGS. 5C and 5D, the seal portion 526 is also partially transitioned between the neutral configuration and the extended configuration. FIGS. 5E and 5F (FIG. 5F being a close up of the distal portion of the sealing introducer assembly 500 as shown in FIG. 5E) show the sealing introducer assembly 500 with the dilator 510 translating the distal tip portion 525 distally such that the seal portion 526 is in the extended configuration (and thus transitioning the sealing introducer assembly 500 to the second configuration for delivery of the introducer assembly 500 to a desired location within a patient's body).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. An introducer assembly comprising:
  an introducer sheath including a body portion and a distal tip portion, the body portion being coupled to the distal tip portion via a seal portion, the introducer sheath defining a lumen; and
  a dilator sized for insertion into the lumen and slideable relative to the body portion between a proximal dilator position and a distal dilator position, the dilator configured to engage the distal tip portion and translate the distal tip portion relative to the body portion from a proximal tip position to a distal tip position as the dilator slides between the proximal dilator position and the distal dilator position,
  wherein the seal portion has a neutral configuration having a first outermost diameter when the distal tip portion is in the proximal tip position, and the seal portion has an extended configuration having a second outermost diameter when the distal tip portion is in the distal tip position, the first outermost diameter being larger than the second outermost diameter, wherein the dilator includes a distal end having a tapered portion, the tapered portion having a proximal end with a proximal taper diameter and a distal end with a distal taper diameter smaller than the proximal taper diameter.

2. The introducer assembly of claim 1, wherein the seal portion is formed of a shape memory material.

3. The introducer assembly of claim 2, wherein the seal portion is formed of braided nitinol.

4. The introducer assembly of claim 2, wherein the seal portion is biased to the neutral configuration in the absence of applied forces.

5. The introducer assembly of claim 4, wherein the seal portion has a disc shape in the neutral configuration.

6. The introducer assembly of claim 5, wherein the seal portion is shaped like an elongated tube in the extended configuration.

7. The introducer assembly of claim 4, wherein the seal portion is cylindrical in the neutral configuration.

8. The introducer assembly of claim 4, wherein the seal portion has a double-disc shape in the neutral configuration.

9. The introducer assembly of claim 1, wherein the body portion of the introducer sheath has an interior body diameter that is greater than the proximal taper diameter and the distal taper diameter.

10. The introducer assembly of claim 9, wherein the distal tip portion has an interior tip diameter that is greater than the distal taper diameter and smaller than the proximal taper diameter.

11. The introducer assembly of claim 1, wherein the dilator includes a dilator lumen extending therethrough, the dilator lumen configured to receive a guidewire therein.

12. The introducer assembly of claim 1, wherein the body portion has an outer diameter that is greater than an outer diameter of the seal portion when the seal portion is in the extended configuration.

13. The introducer assembly of claim 1, wherein the introducer sheath includes a hub at a proximal end of the introducer sheath, dilator configured to be inserted through the hub.

14. The introducer assembly of claim 13, wherein the hub includes a hemostasis valve therein.

15. An introducer assembly comprising:

an introducer sheath including a body portion and a distal tip portion, the body portion being coupled to the distal tip portion via a seal portion, the introducer sheath defining a lumen; and a dilator sized for insertion into the lumen and slideable relative to the body portion between a proximal dilator position and a distal dilator position, the dilator configured to engage the distal tip portion and translate the distal tip portion relative to the body portion from a proximal tip position to a distal tip position as the dilator slides between the proximal dilator position and the distal dilator position, wherein the seal portion has a neutral configuration having a first outermost diameter when the distal tip portion is in the proximal tip position, and the seal portion has an extended configuration having a second outermost diameter when the distal tip portion is in the distal tip position, the first outermost diameter being larger than the second outermost diameter, wherein the dilator includes a first engagement feature on an outer surface thereof and the distal tip portion includes a second engagement feature, the first engagement feature configured to engage the second engagement feature when the dilator slides between the proximal dilator position to the distal dilator position, wherein the dilator includes a distal end having a proximal portion with a proximal diameter and a distal portion with a distal diameter smaller than the proximal diameter.

16. The introducer assembly of claim 15, wherein the dilator includes a first lip at a transition between the proximal and distal portions of the distal end of the dilator, the first lip being the first engagement feature.

17. The introducer assembly of claim 16, wherein the second engagement feature is a second lip formed on the distal tip portion, the second lip being sized and shape to engage the first lip when the dilator slides between the proximal dilator position to the distal dilator position.

18. The introducer assembly of claim 15, wherein the body portion has an outer diameter that is equal to an outer diameter of the seal portion when the seal portion is in the extended configuration.

\* \* \* \* \*